US011000287B2

(12) United States Patent
Tassoni et al.

(10) Patent No.: US 11,000,287 B2
(45) Date of Patent: May 11, 2021

(54) OCCLUSIVE MEDICAL DEVICE SYSTEM

(71) Applicant: BOSTON SCIENTIFIC SCIMED, INC., Maple Grove, MN (US)

(72) Inventors: Nicholas Lee Tassoni, Ramsey, MN (US); Khoi Le, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 115 days.

(21) Appl. No.: 15/998,440

(22) Filed: Aug. 15, 2018

(65) Prior Publication Data
US 2019/0053807 A1    Feb. 21, 2019

Related U.S. Application Data
(60) Provisional application No. 62/545,719, filed on Aug. 15, 2017.

(51) Int. Cl.
*A61B 17/12* (2006.01)
*A61B 90/00* (2016.01)
*A61B 17/00* (2006.01)

(52) U.S. Cl.
CPC .. *A61B 17/12031* (2013.01); *A61B 17/12022* (2013.01); *A61B 17/12145* (2013.01);
(Continued)

(58) Field of Classification Search
CPC ........ A61B 17/12022; A61B 17/12109; A61B 17/12113; A61B 12/1214;
(Continued)

(56) References Cited

U.S. PATENT DOCUMENTS

| 5,117,839 A | 6/1992 | Dance |
| 5,234,437 A | 8/1993 | Sepetka |

(Continued)

FOREIGN PATENT DOCUMENTS

| EP | 2777542 A2 | 9/2014 |
| EP | 2777545 A2 | 9/2014 |

(Continued)

OTHER PUBLICATIONS

International Search Report and Written Opinion dated Dec. 5, 2018 for International Application No. PCT/US2018/000148.
(Continued)

*Primary Examiner* — Ashley L Fishback
*Assistant Examiner* — Uyen N Vo
(74) *Attorney, Agent, or Firm* — Seager, Tufte & Wickhem LLP

(57) ABSTRACT

An occlusive medical device system may include an elongate shaft having a lumen extending longitudinally through a tubular body portion and a plurality of retaining arms extending distally from the tubular body portion. An occlusive medical device may include a proximal tubular mounting portion fixed to an expandable occlusive element. A release wire may be axially translatable between a distal engagement position and a proximal released position, the release wire having a distal engagement portion and a distal retention portion distal of the distal engagement portion. The distal engagement portion may be configured to engage the plurality of retaining arms in the distal engagement position, thereby urging the plurality of retaining arms into releasable engagement with the proximal tubular mounting portion, wherein when the release wire is in the proximal released position, the plurality of retaining arms is deflectable radially inward to disengage from the proximal tubular mounting portion.

12 Claims, 13 Drawing Sheets

(52) U.S. Cl.
CPC ..... *A61B 17/1215* (2013.01); *A61B 17/12113* (2013.01); *A61B 17/12172* (2013.01); *A61B 17/12177* (2013.01); *A61B 2017/00893* (2013.01); *A61B 2017/1205* (2013.01); *A61B 2017/12054* (2013.01); *A61B 2090/037* (2016.02); *A61B 2090/3966* (2016.02)

(58) Field of Classification Search
CPC ........ A61B 17/12145; A61B 17/12159; A61B 17/12168; A61B 17/12172; A61B 17/12177; A61B 17/12031; A61B 17/1204; A61B 17/12036; A61B 2090/037; A61B 2090/3966; A61B 17/1215; A61B 2017/00893; A61B 2017/1205; A61B 2017/12054; A61F 2/95; A61F 2/9522; A61F 2/011; A61F 2002/9505; A61F 2002/9511
See application file for complete search history.

(56) References Cited

U.S. PATENT DOCUMENTS

| | | | |
|---|---|---|---|
| 5,250,071 A | 10/1993 | Palermo | |
| 5,282,478 A | 2/1994 | Fleischhaker, Jr. et al. | |
| 5,304,195 A | 4/1994 | Twyford, Jr. et al. | |
| 5,312,415 A | 5/1994 | Palermo | |
| 5,546,958 A | 8/1996 | Thorud et al. | |
| RE37,117 E | 3/2001 | Palermo | |
| 6,277,125 B1 | 8/2001 | Barry et al. | |
| 6,491,646 B1 | 12/2002 | Blackledge | |
| 7,044,134 B2 | 5/2006 | Khairkhahan et al. | |
| 7,708,755 B2 | 5/2010 | Davis et al. | |
| 7,815,661 B2 | 10/2010 | Mirizzi et al. | |
| 7,896,899 B2 | 3/2011 | Patterson et al. | |
| 8,142,456 B2 | 3/2012 | Rosqueta | |
| 8,236,042 B2 | 8/2012 | Berez et al. | |
| 8,333,786 B2 | 12/2012 | Mirizzi et al. | |
| 8,333,796 B2 | 12/2012 | Tompkins et al. | |
| 8,641,777 B2 | 2/2014 | Strauss et al. | |
| 8,696,701 B2 | 4/2014 | Becking et al. | |
| 8,747,597 B2 | 6/2014 | Rosqueta et al. | |
| 8,795,313 B2 | 8/2014 | Liang et al. | |
| 8,801,746 B1 | 8/2014 | Kreidler et al. | |
| 8,911,487 B2 | 12/2014 | Bennett et al. | |
| 9,017,350 B2 | 4/2015 | Karabey et al. | |
| 9,017,361 B2 | 4/2015 | Karabey et al. | |
| 9,060,773 B2 | 6/2015 | Nguyen et al. | |
| 9,119,948 B2 | 9/2015 | Lee et al. | |
| 9,186,151 B2 | 11/2015 | Tompkins et al. | |
| 9,198,670 B2 | 12/2015 | Hewitt et al. | |
| 9,301,827 B2 | 4/2016 | Strauss et al. | |
| 9,307,999 B2 | 4/2016 | Li et al. | |
| 9,468,442 B2 | 10/2016 | Huynh et al. | |
| 9,498,226 B2 | 11/2016 | Cage et al. | |
| 9,549,740 B2 | 1/2017 | Rees | |
| 9,554,805 B2 | 1/2017 | Tompkins et al. | |
| 2006/0036281 A1 | 2/2006 | Patterson et al. | |
| 2006/0212055 A1 | 9/2006 | Karabey et al. | |
| 2006/0229669 A1 | 10/2006 | Mirizzi et al. | |
| 2006/0282159 A1 | 12/2006 | Taheri | |
| 2007/0135826 A1* | 6/2007 | Zaver et al. | 606/157 |
| 2007/0270903 A1 | 11/2007 | Davis et al. | |
| 2007/0282373 A1 | 12/2007 | Ashby et al. | |
| 2007/0293928 A1 | 12/2007 | Tomlin | |
| 2008/0109059 A1 | 5/2008 | Gordon et al. | |
| 2008/0119891 A1 | 5/2008 | Miles et al. | |
| 2008/0300616 A1 | 12/2008 | Que et al. | |
| 2009/0043331 A1 | 2/2009 | Buiser et al. | |
| 2009/0062838 A1 | 3/2009 | Brumleve et al. | |
| 2009/0062845 A1 | 3/2009 | Tekulve | |
| 2009/0163934 A1 | 6/2009 | Raschdorf, Jr. et al. | |
| 2009/0177261 A1 | 7/2009 | Teoh et al. | |
| 2009/0270978 A1 | 10/2009 | Virkler et al. | |
| 2009/0287291 A1 | 11/2009 | Becking et al. | |
| 2009/0287294 A1 | 11/2009 | Rosqueta et al. | |
| 2010/0106178 A1 | 4/2010 | Obermiller et al. | |
| 2010/0121350 A1 | 5/2010 | Mirigian | |
| 2010/0174269 A1 | 7/2010 | Tompkins et al. | |
| 2011/0166588 A1 | 7/2011 | Connor et al. | |
| 2011/0184454 A1 | 7/2011 | Barry et al. | |
| 2011/0202085 A1 | 8/2011 | Loganathan et al. | |
| 2011/0238147 A1 | 9/2011 | Bennett et al. | |
| 2011/0265943 A1 | 11/2011 | Rosqueta et al. | |
| 2011/0319926 A1 | 12/2011 | Becking et al. | |
| 2012/0046687 A1 | 2/2012 | Trommeter et al. | |
| 2012/0203322 A1 | 8/2012 | Eells | |
| 2012/0283812 A1 | 11/2012 | Lagodzki | |
| 2012/0316598 A1 | 12/2012 | Becking et al. | |
| 2012/0330341 A1 | 12/2012 | Becking et al. | |
| 2012/0330347 A1 | 12/2012 | Becking et al. | |
| 2012/0330348 A1 | 12/2012 | Strauss et al. | |
| 2013/0066360 A1 | 3/2013 | Becking et al. | |
| 2013/0072961 A1 | 3/2013 | Cage et al. | |
| 2013/0085520 A1 | 4/2013 | Liang et al. | |
| 2013/0085522 A1 | 4/2013 | Becking et al. | |
| 2013/0152941 A1 | 6/2013 | Nguyen et al. | |
| 2013/0253572 A1 | 9/2013 | Molaei et al. | |
| 2013/0261730 A1 | 10/2013 | Bose et al. | |
| 2013/0296917 A1 | 11/2013 | Rees | |
| 2013/0331882 A1 | 12/2013 | Tompkins et al. | |
| 2014/0058434 A1 | 2/2014 | Jones et al. | |
| 2014/0058435 A1 | 2/2014 | Jones et al. | |
| 2014/0128907 A1 | 5/2014 | Hui et al. | |
| 2014/0135810 A1 | 5/2014 | Divino et al. | |
| 2014/0135811 A1 | 5/2014 | Divino et al. | |
| 2014/0135812 A1 | 5/2014 | Divino et al. | |
| 2014/0148843 A1 | 5/2014 | Strauss et al. | |
| 2014/0172001 A1 | 6/2014 | Becking et al. | |
| 2014/0236127 A1 | 8/2014 | Lee et al. | |
| 2014/0358175 A1 | 12/2014 | Tompkins et al. | |
| 2015/0005807 A1 | 1/2015 | Lagodzki et al. | |
| 2015/0073524 A1 | 3/2015 | Bennett et al. | |
| 2015/0112378 A1 | 4/2015 | Torp | |
| 2015/0157332 A1 | 6/2015 | Obermiller et al. | |
| 2015/0196304 A1 | 7/2015 | Rabkin et al. | |
| 2015/0230802 A1 | 8/2015 | Lagodzki et al. | |
| 2015/0257763 A1 | 9/2015 | Blum et al. | |
| 2015/0272589 A1 | 10/2015 | Lorenzo | |
| 2015/0297240 A1 | 10/2015 | Divino et al. | |
| 2015/0327868 A1 | 11/2015 | Islak et al. | |
| 2015/0335333 A1 | 11/2015 | Jones et al. | |
| 2015/0342611 A1 | 12/2015 | Leopold et al. | |
| 2015/0343181 A1 | 12/2015 | Bradway et al. | |
| 2016/0008003 A1 | 1/2016 | Kleshinski et al. | |
| 2016/0022445 A1 | 1/2016 | Ruvalcaba et al. | |
| 2016/0030052 A1 | 2/2016 | Cragg et al. | |
| 2016/0166257 A1 | 6/2016 | Allen et al. | |
| 2016/0192942 A1 | 7/2016 | Strauss et al. | |
| 2016/0228123 A1 | 8/2016 | Anderson et al. | |
| 2016/0228124 A1 | 8/2016 | Trommeter et al. | |
| 2016/0228128 A1 | 8/2016 | Connolly | |
| 2016/0317274 A1 | 11/2016 | Liu et al. | |

FOREIGN PATENT DOCUMENTS

| | | | | |
|---|---|---|---|---|
| EP | 3085310 A1 | 10/2016 | | |
| JP | 2016-202905 A | 12/2016 | | |
| JP | 2016537134 A | 12/2016 | | |
| WO | 0232496 A1 | 4/2002 | | |
| WO | 2007047111 A1 | 4/2007 | | |
| WO | 2007070797 A2 | 6/2007 | | |
| WO | 2010030993 A1 | 3/2010 | | |
| WO | 2010098804 A1 | 9/2010 | | |
| WO | 2014145012 A2 | 9/2014 | | |
| WO | 2014145005 A3 | 4/2015 | | |
| WO | WO-2016044647 A2 * | 3/2016 | ....... | A61B 17/12172 |

OTHER PUBLICATIONS

International Search Report & Written Opinion dated Jun. 15, 2018 for International Application No. PCT/US2018/021978.

(56) References Cited

OTHER PUBLICATIONS

PCT Application No. PCT/US2017/061779 International Search Report and Written Opinion, dated Feb. 26, 2018.
International Search Report and Written Opinion dated Jul. 13, 2018 for International Application No. PCT/US2018/028240.

\* cited by examiner

OCCLUSIVE MEDICAL DEVICE SYSTEM

CROSS-REFERENCE TO RELATED APPLICATIONS

This application claims the benefit of priority under 35 U.S.C. § 119 to U.S. Provisional Application Ser. No. 62/545,719, filed Aug. 15, 2017, the entirety of which is incorporated herein by reference.

TECHNICAL FIELD

The present disclosure pertains to medical devices, and methods for manufacturing and/or using medical devices. More particularly, the present disclosure pertains to aspects of an occlusive medical device system and/or means to deliver and release an occlusive medical device.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, occlusive medical devices, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, an occlusive medical device system may comprise an elongate shaft having a tubular body portion, a lumen extending longitudinally through the tubular body portion, and a plurality of retaining arms extending distally from the tubular body portion; an occlusive medical device configured to occlude fluid flow through a vessel lumen, the occlusive medical device including a proximal tubular mounting portion fixed to an expandable occlusive element; and a release wire disposed within the lumen of the tubular body portion and axially translatable between a distal engagement position and a proximal released position, the release wire having a distal engagement portion and a distal retention portion distal of the distal engagement portion. The plurality of retaining arms may extend into the proximal tubular mounting portion. The distal engagement portion of the release wire may be configured to engage the plurality of retaining arms in the distal engagement position, thereby urging the plurality of retaining arms radially outward into releasable engagement with the proximal tubular mounting portion of the occlusive medical device. When the release wire is in the proximal released position, the plurality of retaining arms may be deflectable radially inward to disengage from the proximal tubular mounting portion.

In addition or alternatively, and in a second aspect, the distal retention portion includes a maximum outer extent greater than an inner diameter of the lumen in the distal engagement position.

In addition or alternatively, and in a third aspect, the distal retention portion is configured to axially translate through the lumen from the distal engagement position to the proximal released position.

In addition or alternatively, and in a fourth aspect, the distal retention portion is non-linear.

In addition or alternatively, and in a fifth aspect, the distal retention portion comprises a helical coil.

In addition or alternatively, and in a sixth aspect, the helical coil has a closed pitch.

In addition or alternatively, and in a seventh aspect, the helical coil has an open pitch.

In addition or alternatively, and in an eighth aspect, the distal retention portion comprises a buckled tip.

In addition or alternatively, and in a ninth aspect, the proximal tubular mounting portion includes a plurality of apertures configured to engage the plurality of retaining arms when the release wire is in the distal engagement position.

In addition or alternatively, and in a tenth aspect, each of the plurality of retaining arms includes a protrusion extending radially outward from an outer surface of its respective retaining arm.

In addition or alternatively, and in an eleventh aspect, each protrusion of the plurality of retaining arms engages one of the plurality of apertures of the proximal tubular mounting portion when the release wire is in the distal engagement position.

In addition or alternatively, and in a twelfth aspect, an occlusive medical device system may comprise a microcatheter configured to navigate a vasculature; an elongate shaft having a tubular body portion, a lumen extending longitudinally through the tubular body portion, and a plurality of retaining arms extending distally from the tubular body portion; an occlusive medical device configured to occlude fluid flow through a vessel lumen, the occlusive medical device including a proximal tubular mounting portion fixed to an expandable occlusive element; and a release wire disposed within the lumen of the tubular body portion and axially translatable between a distal engagement position and a proximal released position, the release wire having a distal engagement portion and a distal retention portion distal of the distal engagement portion. The plurality of retaining arms may extend into the proximal tubular mounting portion. The distal engagement portion of the release wire may be configured to engage the plurality of retaining arms in the distal engagement position, thereby urging the plurality of retaining arms radially outward into releasable engagement with the proximal tubular mounting portion of the occlusive medical device. When the release wire is in the proximal released position, the plurality of retaining arms may be deflectable radially inward to disengage from the proximal tubular mounting portion. The elongate shaft may be slidably disposed within a lumen of the microcatheter.

In addition or alternatively, and in a thirteenth aspect, the occlusive medical device is expandable from a delivery configuration to a deployed configuration.

In addition or alternatively, and in a fourteenth aspect, the occlusive medical device is disposed within a distal end of the lumen of the microcatheter in the delivery configuration.

In addition or alternatively, and in a fifteenth aspect, when the release wire is in the proximal released position and the plurality of retaining arms is disengaged from the proximal tubular mounting portion, the occlusive medical device is released from the elongate shaft.

In addition or alternatively, and in a sixteenth aspect, an occlusive medical device system may comprise a microcatheter configured to navigate a vasculature; an elongate shaft slidably disposed within a lumen of the microcatheter, the elongate shaft having a lumen extending through a tubular body portion from a proximal end of the elongate shaft to a distal end of the elongate shaft; an occlusive medical device configured to occlude fluid flow through a vessel lumen, the occlusive medical device being releasably connected to the elongate shaft; and a release wire disposed within the lumen of the tubular body portion and axially translatable between a distal engagement position and a proximal released position, the release wire having a distal engagement portion and a non-linear distal retention portion distal of the distal engagement portion. The release wire may secure the occlusive medical device to the distal end of the elongate shaft when the release wire is disposed within at least a portion of the occlusive medical device.

In addition or alternatively, and in a seventeenth aspect, the occlusive medical device system may further comprise an attachment mechanism disposed between the distal end of the elongate shaft and a proximal end of the occlusive medical device. The attachment mechanism may comprise a first part having a first longitudinal lumen configured to slidably receive the release wire, and a second part having a second longitudinal lumen configured to slidably receive the release wire. The first part may be fixedly attached to the distal end of the elongate shaft and the second part may be fixedly attached to the proximal end of the occlusive medical device.

In addition or alternatively, and in an eighteenth aspect, in the distal engagement position, the non-linear distal retention portion is disposed distal of the second part, and the non-linear distal retention portion defines a maximum outer extent greater than an inner diameter of the second longitudinal lumen.

In addition or alternatively, and in a nineteenth aspect, the first part and the second part are configured to interlock with each other such that relative axial translation between the first part and the second part is prevented when the first part abuts the second part and the first longitudinal lumen is aligned coaxially with the second longitudinal lumen.

In addition or alternatively, and in a twentieth aspect, the first part and the second part are configured to interlock with each other such that relative lateral translation between the first part and the second part is prevented when the first part abuts the second part, the first longitudinal lumen is aligned coaxially with the second longitudinal lumen, and the release wire is slidably engaged with the first longitudinal lumen and the second longitudinal lumen.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
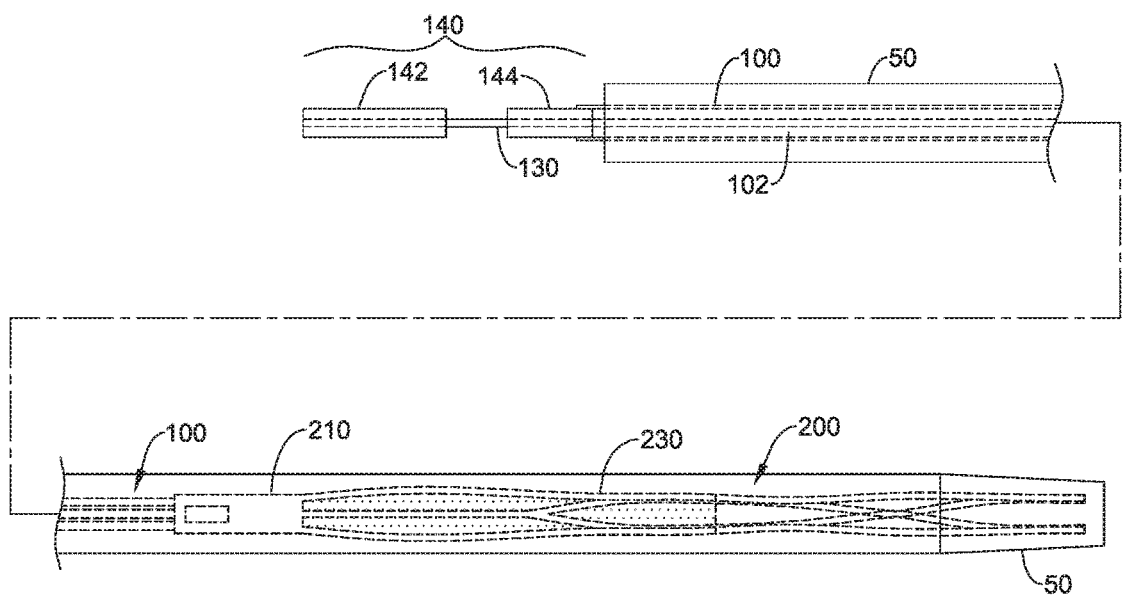
FIG. 1 illustrates an example occlusive medical device system including an occlusive medical device in a delivery configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

Figure 2:
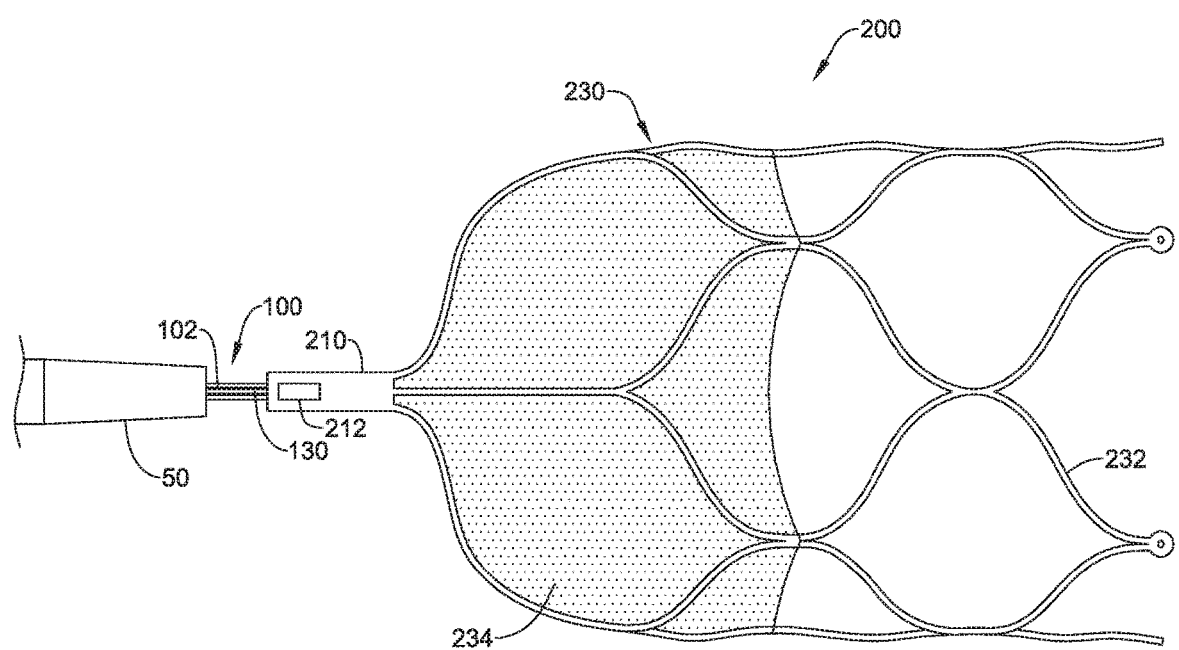
FIG. 2 illustrates the occlusive medical device system including the occlusive medical device in an expanded configuration.

FIGS. 1 and 2 illustrate an example occlusive medical device system. Certain details of various elements of the occlusive medical device system are described in greater detail below with reference to FIGS. 3-9. The occlusive medical device system may comprise a microcatheter 50 having a lumen extending through the microcatheter 50. The occlusive medical device system may comprise an elongate shaft 100 slidably disposed within the lumen of the microcatheter 50. The elongate shaft 100 may include a proximal end, a distal end, and a lumen 102 extending longitudinally through a tubular body portion of the elongate shaft 100 along a longitudinal axis of the elongate shaft 100. Additionally, the occlusive medical device system may comprise a release wire 130 slidably disposed within the lumen 102 of the elongate shaft 100 and axially translatable between a distal engagement position (e.g., FIGS. 3 and 7) and a proximal released position (e.g., FIGS. 8-9), for reasons that will become apparent. In some embodiments, a proximal portion and/or proximal end of the release wire 130 may be releasably secured to the proximal end of the elongate shaft 100, for example, using (but not limited to) a perforated polymer joint, a dissimilar polymer joint, a frangible joint, etc. Some suitable but non-limiting materials for the microcatheter 50, the elongate shaft 100, and/or the release wire 130, for example metallic materials, polymer materials, composite materials, etc., are described below.

The occlusive medical device system may comprise an occlusive medical device 200 configured to occlude fluid and/or blood flow through a vessel lumen (e.g., an artery, etc.). The occlusive medical device 200 may include a proximal tubular mounting portion 210 fixed to, fixedly attached to, and/or integrally formed with an expandable occlusive element 230. The proximal tubular mounting portion 210 may include a plurality of apertures 212, which will be explained in greater detail below. The occlusive medical device 200 may have and/or define a longitudinal axis extending from the proximal tubular mounting portion 210 through and/or along the expandable occlusive element 230. In some embodiments, at least a portion of the elongate shaft 100 may extend into and/or releasably engage with the proximal tubular mounting portion 210 of the occlusive medical device 200. The occlusive medical device 200 and/or the expandable occlusive element 230 may be radially expandable and/or longitudinally foreshortenable from a delivery configuration (e.g., FIG. 1) to an expanded deployed configuration (e.g., FIG. 2). The expandable occlusive element 230 may comprise a support frame 232 and an occlusive membrane 234 fixedly attached to, encapsulating, and/or surrounding at least a portion of the support frame 232. Alternatively, the occlusive medical device 200 may be and/or include a vascular plug, an embolic coil, or other suitable occlusive medical device.

In some embodiments, the occlusive medical device 200 and/or the expandable occlusive element 230 may be disposed within a distal portion and/or a distal end of the microcatheter 50 in the delivery configuration, as seen in FIG. 1. After advancing and/or navigating the occlusive medical device 200 to a target site or area of interest, the elongate shaft 100 and/or the occlusive medical device 200 may be advanced distally out of the microcatheter 50, and/or the microcatheter 50 may be retracted proximally as the elongate shaft 100 and/or the occlusive medical device 200 is held in a fixed position, (e.g., the elongate shaft 100 and/or the occlusive medical device 200 may be translated longitudinally relative to the microcatheter 50) to expose the occlusive medical device 200. In at least some embodiments, the support frame 232 may be formed from a self-expanding material configured to automatically expand toward and/or to the expanded configuration when unconstrained (e.g., the support frame 232 may be configured to shift from the delivery configuration to the expanded deployed configuration), as seen in FIG. 2. In some embodiments, the support frame 232 may be formed from a shape memory material or other material configured with a "trigger" (e.g., temperature, electrical current, etc.) such that the support frame 232 may remain in the delivery configuration until the support frame 232 is "activated", at which time the support frame 232 may shift to the expanded configuration. Other embodiments are also envisioned which may utilize mechanical expansion and/or a supporting expansion member to shift the occlusive medical device 200, the expandable occlusive element 230, and/or the support frame 232 from the delivery configuration to the expanded configuration.

In some embodiments, the expandable occlusive element 230 and/or the support frame 232 may include and/or comprise at least one strut, support, and/or member. In some embodiments, the expandable occlusive element 230 and/or the support frame 232 may include and/or comprise a plurality of struts, supports, and/or members interconnected, joined together, and/or integrally formed with each other. In at least some embodiments, the expandable occlusive element 230 and/or the support frame 232 may include a generally closed first end proximate the proximal tubular mounting portion 210 of the occlusive medical device 200 and a generally open second end opposite the generally closed first end, wherein the expandable occlusive element 230 and/or the support frame 232 expands radially outward from and opens away from the proximal tubular mounting portion 210 of the occlusive medical device 200. In some embodiments, the expandable occlusive element 230 and/or the support frame 232 may include a generally closed first end proximate the proximal tubular mounting portion 210 of the occlusive medical device 200 and a generally closed second end opposite the generally closed first end, wherein a middle portion of the expandable occlusive element 230 and/or the support frame 232 expands radially outward from and/or between the generally closed first end and the generally closed second end. The expandable occlusive element 230 and/or the support frame 232 may have and/or define a longitudinal length along a longitudinal axis of the occlusive medical device 200. Some suitable but non-limiting materials for the expandable occlusive element 230 and/or the support frame 232, for example metallic materials, polymer materials, composite materials, etc., are described below.

As mentioned above, the occlusive membrane 234 may be fixedly attached to, encapsulate, and/or surround at least a portion of the support frame 232. In some embodiments, the occlusive membrane 234 may be disposed on and/or attached to an inside surface of the expandable occlusive element 230 and/or the support frame 232, an outside surface of the expandable occlusive element 230 and/or the support frame 232, and/or may extend between individual struts, supports, and/or members of the expandable occlusive element 230 and/or the support frame 232. In some embodiments, the occlusive membrane 234 may include a generally closed first end proximate the proximal tubular mounting portion 210 of the occlusive medical device 200 and a generally open second end opposite the generally closed first end. In some embodiments, the occlusive membrane 234 may include a generally closed first end proximate the proximal tubular mounting portion 210 of the occlusive medical device 200 and a generally closed second end opposite the generally closed first end. In some embodiments, the generally closed first end of the occlusive membrane 234 may be disposed at and/or may be fixedly attached to the proximal tubular mounting portion 210 of the occlusive medical device 200. In some embodiments, the generally closed first end of the occlusive membrane 234 may be disposed distal of the proximal tubular mounting portion 210 of the occlusive medical device 200. In some embodiments, the occlusive membrane 234 may extend along a portion of the longitudinal length of the expandable occlusive element 230 and/or the support frame 232. For example, the second end of the occlusive membrane 234 may be disposed between the first end of the expandable occlusive element 230 and/or the support frame 232 and the second end of the expandable occlusive element 230 and/or the support frame 232. In some embodiments, the second end of the occlusive membrane 234 may be substantially straight and/or arranged in a planar manner normal to the longitudinal axis of the occlusive medical device 200. In some embodiments, the second end of the occlusive membrane 234 may be substantially scalloped and/or have a variable longitudinal length along and/or relative to the longitudinal axis of the occlusive medical device 200. In some embodiments, the occlusive membrane 234 may extend along the entire longitudinal length of the expandable occlusive element 230 and/or the support frame 232.

In some embodiments, the occlusive membrane 234 may be substantially non-porous and/or impermeable to fluid. For example, in some embodiments, blood or other fluid(s) may be unable to pass through the occlusive membrane 234. As such, when the occlusive medical device 200 and/or the expandable occlusive element 230 is deployed within the vessel lumen (e.g., an artery, etc.) in the expanded configuration, the expandable occlusive element 230, the support frame 232, and/or the occlusive membrane 234 may extend across the vessel lumen and substantially and/or completely block and/or occlude fluid and/or blood flow through the vessel lumen. In some embodiments, the occlusive membrane 234 may include and/or be formed from a knitted, woven, and/or porous material having an impermeable coating and/or layer of material (e.g., polymeric material, etc.) formed thereon and/or thereover. In some embodiments, the occlusive membrane 234 may include and/or be formed from a knitted, woven, and/or porous material where blood quickly coagulates to form an impermeable barrier. Some suitable but non-limiting materials for the occlusive membrane 234, for example metallic materials, polymer materials, composite materials, textile materials, etc., are described below.

In some embodiments, the occlusive medical device system may include a securement member 140 fixedly attached to and/or extending proximally from a proximal end of the elongate shaft 100, and fixedly attached to a proximal end of the release wire 130. The securement member 140 may include a proximal portion 142, a distal portion 144, and a wall extending from a proximal end of the securement member 140 to a distal end of the securement member 140. In at least some embodiments, the proximal portion 142 of the securement member 140 may be integrally formed with the distal portion 144 of the securement member 140 as a single unitary structure. Some suitable but non-limiting materials for the securement member 140, for example metallic materials, polymer materials, composite materials, etc., are described below.

In some embodiments, the proximal portion 142 of the securement member 140 may be configured to disengage from the distal portion 144 of the securement member 140. The proximal portion 142 of the securement member 140 may be fixedly attached to the proximal end of the release wire 130. The distal portion 144 of the securement member 140 may be fixedly attached to the proximal end of the elongate shaft 100. In at least some embodiments, an outer surface of the distal portion 144 of the securement member 140 may be fixedly attached to an inner surface of the elongate shaft 100 (e.g., a surface defining the lumen 102). Alternatively, in some embodiments, an inner surface of the distal portion 144 of the securement member 140 may be fixedly attached to an outer surface of the elongate shaft 100. In some embodiments, the proximal portion 142 of the securement member 140 may be releasably secured to and/or configured to disengage from the distal portion 144 of the securement member 140 at a joint. In some embodiments, the joint may be a perforation, a dissimilar polymer joint, a frangible link, or other releasable securement feature formed in the wall of the securement member 140.

In at least some embodiments, the securement member 140 may prevent axial translation of the release wire 130 relative to the elongate shaft 100 and/or the occlusive medical device 200 prior to disengagement of the proximal portion 142 of the securement member 140 from the distal portion 144 of the securement member 140. Disengaging the proximal portion 142 of the securement member 140 from the distal portion 144 of the securement member 140 may permit the release wire 130 to axially translate relative to the distal portion 144 of the securement member 140 and/or the elongate shaft 100. In other words, the wall of the distal portion 144 of the securement member 140 may define a lumen, wherein the release wire 130 is slidably disposed within the lumen of the distal portion 144 of the securement member 140. Upon disengagement of the proximal portion 142 of the securement member 140 from the distal portion 144 of the securement member 140, axial translation of the proximal portion 142 relative to the distal portion 144 of the securement member 140 and/or the elongate shaft 100 may translate the release wire 130 relative to the elongate shaft 100 and/or the distal portion 144 of the securement member 140 to release the occlusive medical device 200 from the distal end of the elongate shaft 100.

The release wire 130, in the distal engagement position, urges the plurality of retaining arms 120 into releasable engagement with the proximal tubular mounting portion 210 of the occlusive medical device 200 when the proximal portion 142 of the securement member 140 is engaged with the distal portion 144 of the securement member 140. For example, when the proximal portion 142 of the securement member 140 is disengaged and/or separated from the distal portion 144 of the securement member 140, the release wire 130 is translated in a proximal direction relative to the elongate shaft 100 to the proximal released position, thereby permitting the plurality of retaining arms 120 to deflect radially inward and disengage from the proximal tubular mounting portion 210. In some embodiments, the release wire 130 may be slidably disposed within the distal portion 144 of the securement member 140, the elongate shaft 100, the lumen 102, the plurality of retaining arms 120, and at least a portion of the proximal tubular mounting portion 210 and/or the occlusive medical device 200.

In use, the elongate shaft 100 may have sufficient length to reach from the target site or area of interest to a position outside of the patient where the occlusive medical device system may be manipulated by an operator (e.g., clinician, physician, user, etc.). The operator of the occlusive medical device system may then place a first hand on the distal portion 144 of the securement member 140 and a second hand on the proximal portion 142 of the securement member 140. The proximal portion 142 of the securement member 140 may be configured to disengage from the distal portion 144 of the securement member 140 at a location proximal of the microcatheter 50. In at least some embodiments, the proximal portion 142 of the securement member 140 may be disengaged from the distal portion 144 of the securement member 140 by bending, twisting, and/or pulling the proximal portion 142 of the securement member 140 relative to the distal portion 144 of the securement member 140. In some embodiments, disengaging the proximal portion 142 of the securement member 140 from the distal portion 144 of the securement member 140 may include moving the proximal portion 142 of the securement member 140 relative to the distal portion 144 of the securement member 140 to separate the proximal portion 142 of the securement member 140 from the distal portion 144 of the securement member 140. In some embodiments, disengaging the proximal portion 142 of the securement member 140 from the distal portion 144 of the securement member 140 may include using an external device (e.g., a torque device, an external handle, etc.) to move the proximal portion 142 of the securement member 140 relative to the distal portion 144 of the securement member 140.

In some embodiments, the joint may include a series of apertures (e.g., perforation) extending through the wall of the securement member 140. In some embodiments, the joint may extend circumferentially about an entire circumference of the wall of the securement member 140. In some embodiments, the joint may extend partially and/or intermittently about the entire circumference of the wall of the securement member 140. In some embodiments, the joint may be generally oriented and/or positioned within a plane perpendicular to a longitudinal axis of the securement member 140. In some embodiments, the joint may be oriented and/or positioned within or along a plane at an oblique angle to the longitudinal axis of the securement member 140. Other, for example non-planar, configurations are also possible. The proximal portion 142 of the securement member 140 is disposed proximal of the joint and the distal portion 144 of the securement member 140 is disposed distal of the joint. As mentioned above, the proximal portion 142 of the securement member 140 may be releasably secured to and/or configured to disengage from the distal portion 144 of the securement member 140 at the joint formed in the wall of the securement member 140.

Figure 3:
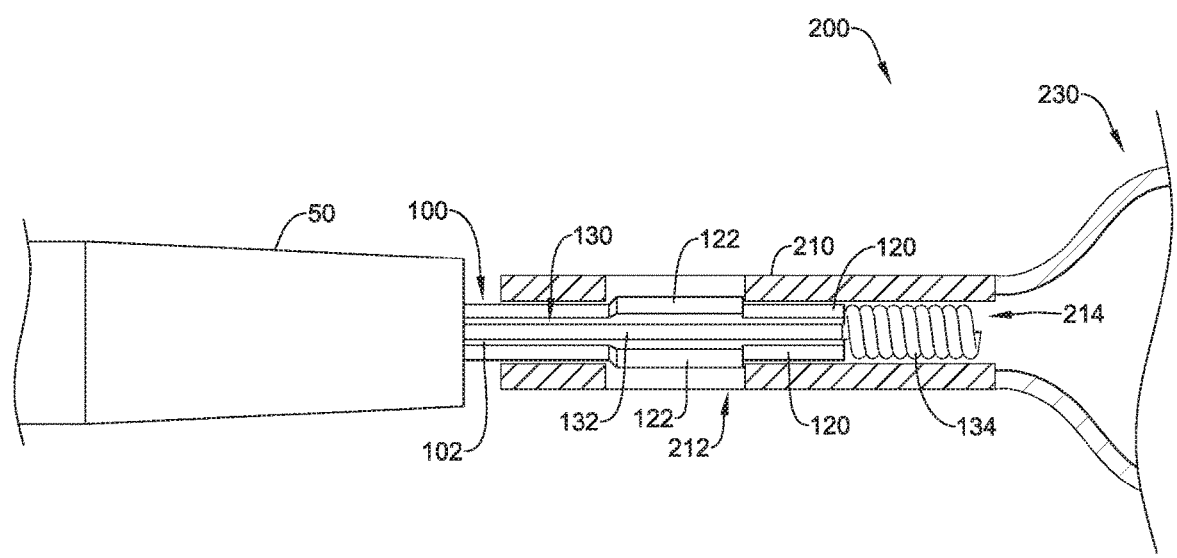
FIG. 3 is a partial cut-away view of the occlusive medical device system of FIG. 2.

FIG. 3 illustrates an example attachment mechanism of the occlusive medical device system. As mentioned above, the elongate shaft 100 may include a proximal end, a distal end, and a lumen 102 extending longitudinally through a tubular body portion of the elongate shaft 100. The elongate shaft 100 may further comprise and/or include a plurality of retaining arms 120 extending distally from the tubular body portion. In some embodiments, the plurality of retaining arms 120 may be biased radially inward. In some embodiments, the plurality of retaining arms 120 may be self-biased radially inward. In some embodiments, the plurality of retaining arms 120 may be configured to deflect radially inward when unconstrained and/or when not biased radially outwardly by the release wire 130 as described herein. In some embodiments, the plurality of retaining arms 120 may comprise two retaining arms, three retaining arms, four retaining arms, or another suitable number of retaining arms.

In some embodiments, the plurality of retaining arms 120 may be arranged circumferentially about the longitudinal axis of the elongate shaft 100. In some embodiments, a longitudinally-extending slot may extend between adjacent retaining arms 120, thereby radially, angularly, and/or circumferentially spacing apart the adjacent retaining arms 120. For example, centerlines (arranged generally parallel to the longitudinal axis of the elongate shaft 100) of each of the plurality of retaining arms 120 may be arranged and/or spaced apart at equal and/or regular radial, angular, and/or circumferential intervals (e.g., 90 degrees apart, 120 degrees apart, etc.) about the longitudinal axis of the elongate shaft 100. Alternatively, in some embodiments, centerlines (arranged generally parallel to the longitudinal axis of the elongate shaft 100) of each of the plurality of retaining arms 120 may be arranged and/or spaced apart at unequal and/or irregular radial, angular, and/or circumferential intervals about the longitudinal axis of the elongate shaft 100, with appropriate changes to the spacing (e.g., size of longitudinally-extending slot, etc.) of the plurality of retaining arms 120 to permit the desired inward deflection of the plurality of retaining arms 120, as described herein. The plurality of retaining arms 120 may be formed and/or made by one or more of a variety of suitable means including, but not limited to, machining, cutting (e.g., laser, water jet, etc.), electro discharge machining, grinding, etc.

Figure 7:
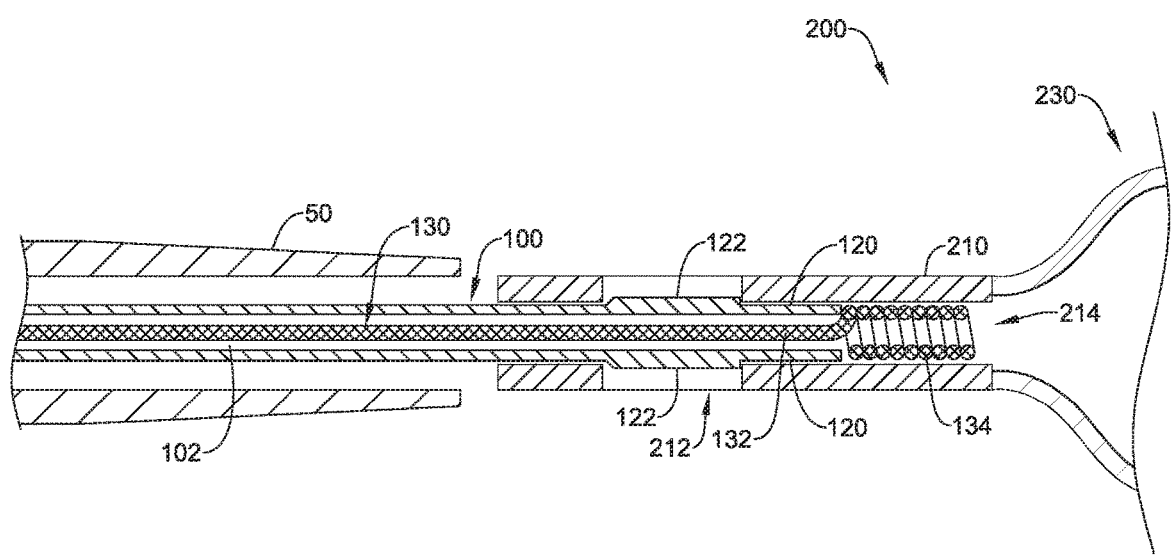
FIGS. 7-9 are cross-sectional views illustrating the release of the occlusive medical device of FIGS. 1-2.
Figure 8:
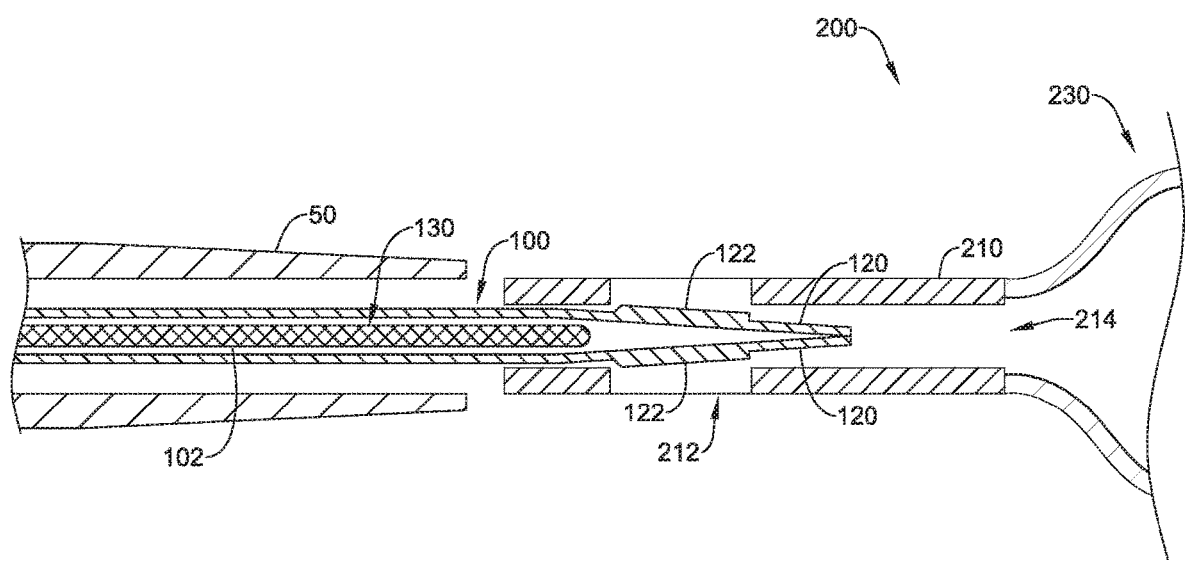
Figure 9:
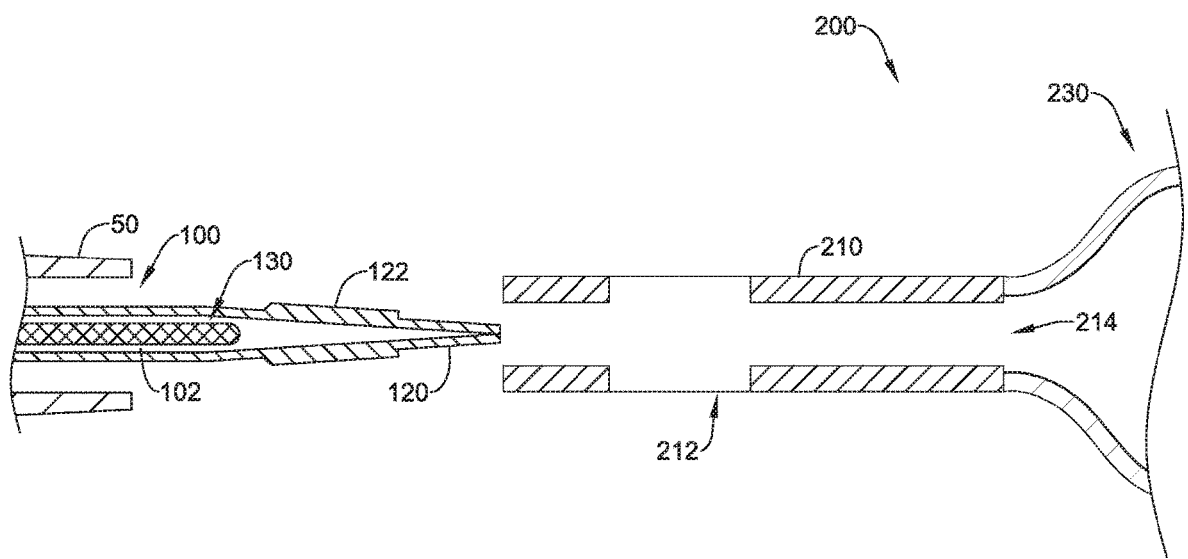

The elongate shaft 100 may include the release wire 130 slidably disposed within the lumen 102 of the tubular body portion of the elongate shaft 100 and axially translatable between the distal engagement position (e.g., FIGS. 3 and 7) and the proximal released position (e.g., FIGS. 8-9). The release wire 130 may have a distal engagement portion 132 and a distal retention portion 134 disposed distal of and/or extending distally from the distal engagement portion 132. The distal retention portion 134 of the release wire 130 may be substantially non-linear.

As seen in the figures, the plurality of retaining arms 120 may extend into a lumen 214 extending longitudinally through the proximal tubular mounting portion 210. The distal engagement portion 132 of the release wire 130 may be configured to engage the plurality of retaining arms 120 in the distal engagement position (e.g., FIGS. 3 and 7), thereby urging the plurality of retaining arms 120 radially outward into releasable engagement with the proximal tubular mounting portion 210 of the occlusive medical device 200 such that proximal axial translation of the elongate shaft 100 relative to the proximal tubular mounting portion 210 is prevented. When the release wire 130 is axially translated to and/or disposed in the proximal released position (e.g., FIGS. 8-9), wherein the distal retention portion 134 has been pulled proximally through the plurality of retaining arms 120, the plurality of retaining arms 120 may be deflectable radially inward to disengage from the proximal tubular mounting portion 210 such that proximal axial translation of the elongate shaft 100 relative to the proximal tubular mounting portion 210 is permitted. In some embodiments, when the release wire 130 is axially translated to and/or disposed in the proximal released position (e.g., FIGS. 8-9), the plurality of retaining arms 120 may be biased and/or self-biased radially inward and disengage from the proximal tubular mounting portion 210 such that proximal axial translation of the elongate shaft 100 relative to the proximal tubular mounting portion 210 is permitted.

In at least some embodiments, each of the plurality of retaining arms 120 may include a protrusion 122 proximate the distal end thereof and extending radially outward from an outer surface and/or an outwardly-facing surface of its respective retaining arm 120. In some embodiments, the protrusion 122 on each of the plurality of retaining arms 120 may be urged radially outward into releasable engagement with the proximal tubular mounting portion 210 of the occlusive medical device 200 when the release wire 130 is in the distal engagement position (e.g., FIG. 7). For example, when the release wire 130 is in the distal engagement position, the plurality of retaining arms 120 may be prevented from deflecting radially inward toward the longitudinal axis of the elongate shaft 100. The protrusion 122 of each of the plurality of retaining arms 120 may be formed on and/or added to its respective retaining arm using one or more suitable means including, but not limited to, adhesive, soldering, welding, grinding, electro discharge machining, etc.

As illustrated in FIGS. 3 and 7-9, the protrusions 122 of the plurality of retaining arms 120 may be formed as rectilinear and/or elongated protuberances having a longitudinal dimension arranged generally parallel to the longitudinal axis of the elongate shaft 100. Other shapes, orientations, and/or arrangements are also contemplated. The proximal tubular mounting portion 210 may include the plurality of apertures 212 extending from an outer surface of the proximal tubular mounting portion 210 through to the lumen 214 extending through the proximal tubular mounting portion 210, as seen in FIG. 3 for example. The plurality of apertures 212 may be configured to engage the plurality of retaining arms 120 when the release wire 130 is in the distal engagement position (e.g., FIGS. 3 and 7). In some embodiments, each of the protrusions 122 of the plurality of retaining arms 120 engages one of the plurality of apertures 212 of the proximal tubular mounting portion 210 when the release wire 130 is in the distal engagement position (e.g., FIGS. 3 and 7). When the release wire 130 is in the proximal released position (e.g., FIGS. 8-9), the plurality of retaining arms 120 may be deflectable radially inward and the protrusions 122 may disengage from the plurality of apertures 212 of the proximal tubular mounting portion 210. In some embodiments, when the release wire 130 is in the proximal released position (e.g., FIGS. 8-9), the plurality of retaining arms 120 may be biased and/or self-biased radially inward and the protrusions 122 may thereby disengage from the plurality of apertures 212 of the proximal tubular mounting portion 210. The plurality of apertures 212 may have a corresponding shape (e.g., rectangular, rectilinear, other shapes, etc.) configured to complement and/or engage with the protrusions 122 of the plurality of retaining arms 120.

In an alternative configuration, the arrangement(s) described above may be inverted, wherein the features of the distal end of the elongate shaft 100 (e.g., the plurality of retaining arms 120, the protrusion(s) 122, etc.) may be disposed on and/or be formed with a proximal end of the occlusive medical device 200, and the features of the proximal tubular mounting portion 210 (e.g., the lumen 214, the plurality of apertures 212, etc.) may be disposed on and/or be formed with a distal end of the elongate shaft 100. Other functionality may remain substantially the same as described above, with the plurality of retaining arms (now of the occlusive medical device) extending into the proximal tubular mounting portion (now of the elongate shaft), and the release wire 130 urging the plurality of retaining arms into releasable engagement with the proximal tubular mounting portion in the distal engagement position. Proximal translation of the release wire from the distal engagement position to the proximal release position may permit the plurality of retaining arms to disengage from the proximal tubular mounting portion and release the occlusive medical device from the elongate shaft.

Figure 4:
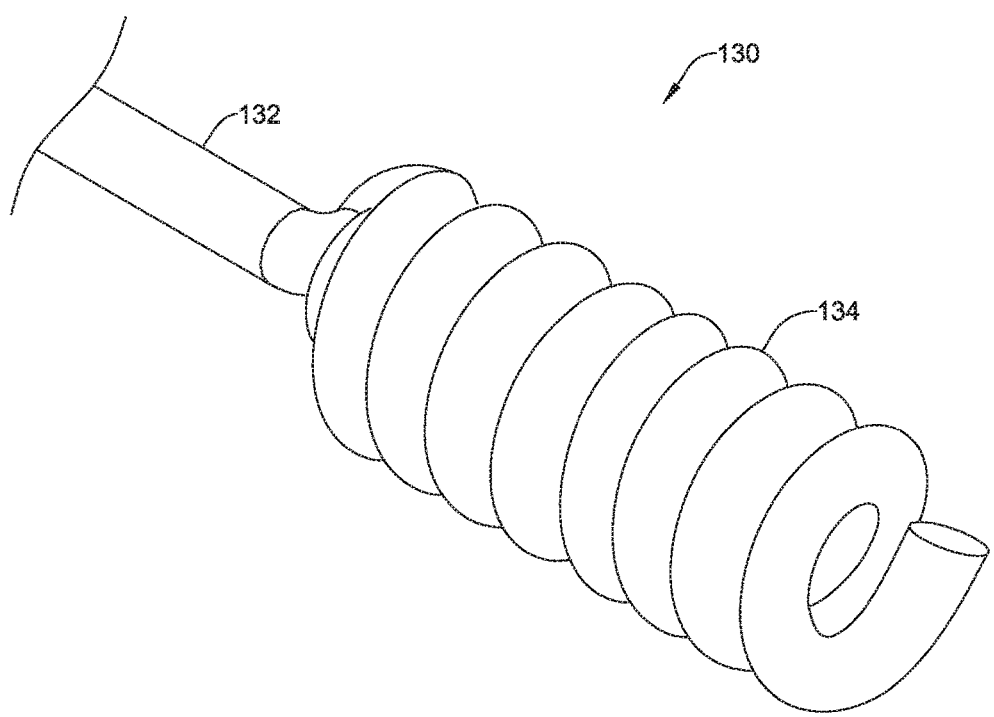
FIG. 4 illustrates an example release wire of the occlusive medical device system.
Figure 5:
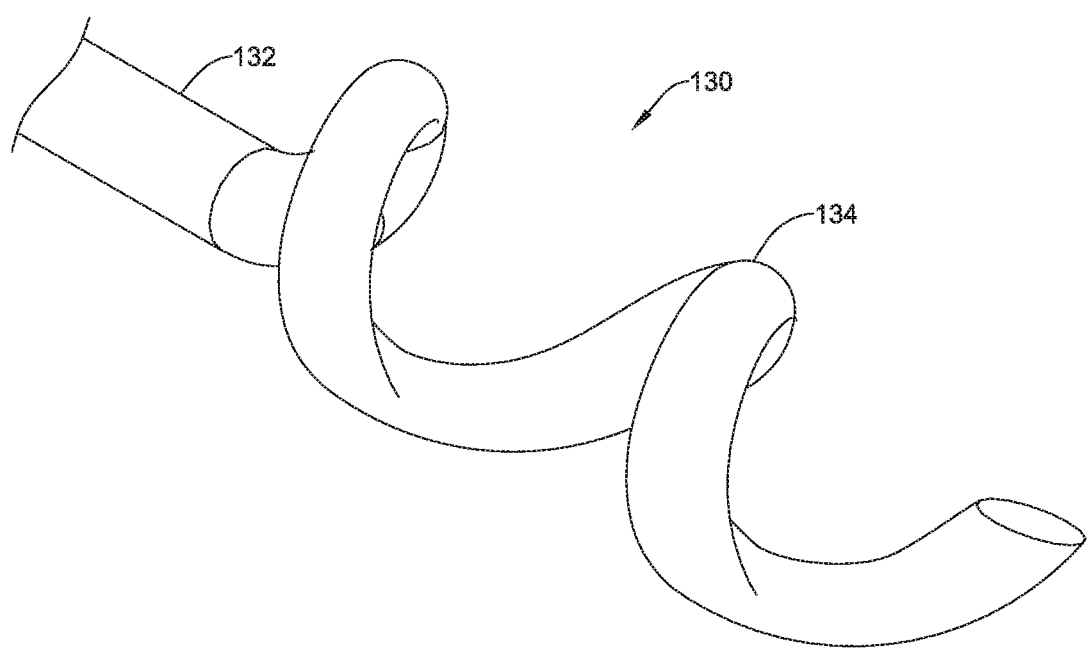
FIG. 5 illustrates an example release wire of the occlusive medical device system.
Figure 6:
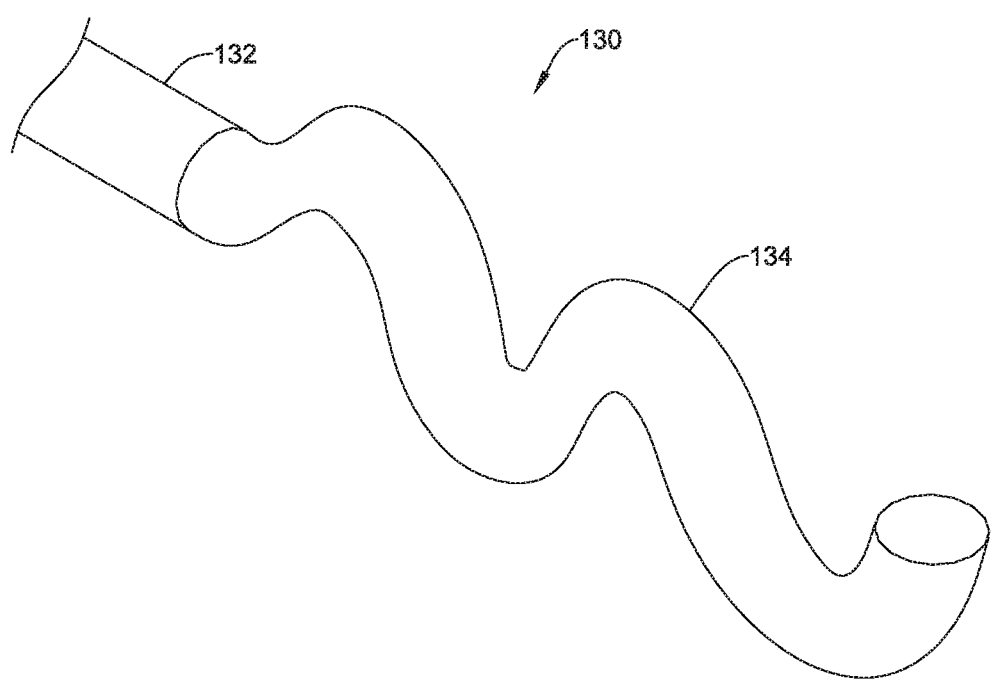
FIG. 6 illustrates an example release wire of the occlusive medical device system.

Turning to FIGS. 4-6, an example release wire 130 is illustrated. As discussed above, the release wire 130 may include a distal engagement portion 132 and a distal retention portion 134. The distal retention portion 134 may be non-linear, wherein the distal retention portion 134 gives the release wire 130 a longer effective length distal of the distal engagement portion 132 relative to a linear or straight release wire having the same overall length. In some embodiments, the longer effective length of the distal engagement portion 132 may prevent accidental and/or premature detachment of the occlusive medical device 200 from the elongate shaft 100 and/or the plurality of retaining arms 120. For example, in some embodiments, visualization of the occlusive medical device 200 after initial placement, deployment, and/or unsheathing may reveal incorrect or suboptimal positioning of the occlusive medical device. Re-sheathing the occlusive medical device 200 into the microcatheter 50 may result in contact and/or interference between the occlusive medical device 200 and the microcatheter 50 that can cause the elongate shaft 100 to stretch, thereby resulting in relative axial movement between the elongate shaft 100 and the release wire 130. Too much stretch could pull the release wire 130 through the plurality of retaining arms 120 to the proximal released position (e.g., (FIGS. 8-9) and subsequent release of the occlusive medical device 200 at an unintended position. Accordingly, the release wire 130 may have a non-linear distal retention portion 134 to provide an increased effective length of the distal engagement portion 132.

In at least some embodiments, the distal retention portion 134 may comprise a helical coil. In some embodiments, the helical coil may have a closed pitch, as seen in FIG. 4 for example. In some embodiments, the helical coil may have an open pitch, as seen in FIG. 5 for example. In some embodiments, the distal retention portion 134 may comprise a buckled tip, as seen in FIG. 6 for example. The buckled tip may include a two-dimensional zig-zag arrangement, wherein the buckled tip undulates back and forth in a mostly planar orientation to increase the effective length of the distal engagement portion 132. In some embodiments, the distal retention portion 134 may require 5-100 gf (gram-force) to elongate, straighten, and/or uncoil the distal retention portion 134 in order to axially translate the release wire 130 to the proximal released position. Although the occlusive medical device system(s) of the disclosure are illustrated with the release wire 130 of FIG. 4, this arrangement is merely exemplary and the release wire 130 shown in FIGS. 5-6 may be used interchangeably therewith.

In addition or alternatively, in some embodiments, the distal retention portion 134 may provide an increased degree of stretch resistance to the elongate shaft 100 due to an increased amount of force required to elongate, straighten, and/or uncoil the distal retention portion 134 of the release wire 130 and/or to axially translate the release wire 130 to the proximal released position. For example, the distal retention portion 134 may require 100-300 gf (gram-force) to elongate, straighten, and/or uncoil the distal retention portion 134 in order to axially translate the release wire 130 to the proximal released position. In some embodiments, the increased amount of force required to elongate, straighten, and/or uncoil the distal retention portion 134 of the release wire 130 and/or to axially translate the release wire 130 to the proximal released position may be achieved by forming the release wire 130 from a larger outer diameter (O.D.) wire, by forming the release wire 130 with a tighter/smaller pitch between adjacent coils (e.g., a closed pitch vs. an open pitch), and/or winding the distal retention portion 134 to a smaller maximum extent (e.g., a smaller O.D.). As such, the distal retention portion 134 may act as a stretch-resistance feature that resists relative axial movement between the elongate shaft 100 and the release wire 130, and help prevent premature detachment and/or release of the occlusive medical device 200. In at least some embodiments, the distal retention portion 134 may provide both a longer effective length of the distal engagement portion 132 and a stretch-resistance feature as described herein.

FIGS. 7-9 illustrate aspects of a method or process of releasing the occlusive medical device 200 from the occlusive medical device system. The occlusive medical device system may include the microcatheter 50 configured to navigate a vasculature. The occlusive medical device system may include the elongate shaft 100, wherein the elongate shaft 100 may be slidably disposed within a lumen of the microcatheter 50. As mentioned above with respect to FIG. 3, the plurality of retaining arms 120 may extend into the lumen 214 extending longitudinally through the proximal tubular mounting portion 210. The distal engagement portion 132 of the release wire 130 may be configured to engage the plurality of retaining arms 120 in the distal engagement position, as shown in FIG. 7, thereby urging the plurality of retaining arms 120 radially outward into releasable engagement with the proximal tubular mounting portion 210 of the occlusive medical device 200 such that proximal axial translation of the elongate shaft 100 relative to the proximal tubular mounting portion 210 is prevented. The proximal tubular mounting portion 210 includes the plurality of apertures 212 configured to engage the plurality of retaining arms 120 when the release wire 130 is in the distal engagement position. As mentioned above, each of the plurality of retaining arms 120 includes a protrusion 122 extending radially outward from the outer surface of its respective retaining arm 120. In at least some embodiments, each of the protrusions 122 of the plurality of retaining arms 120 engages one of the plurality of apertures 212 of the proximal tubular mounting portion 210 when the release wire 130 is in the distal engagement position.

As shown in FIG. 7 for example, the distal retention portion 134 of the release wire 130 may include a maximum outer extent greater than an inner diameter of the lumen 102 of the elongate shaft 100 when the release wire 130 is in the distal engagement position. Additionally, the distal retention portion 134 and/or the release wire 130 may be configured to axially translate through the lumen 102 and/or the plurality of retaining arms 120 from the distal engagement position to the proximal released position, shown in FIGS. 8 and 9 for example.

When the release wire 130 is axially translated to and/or disposed in the proximal released position (e.g., FIG. 8), wherein the distal retention portion 134 has been pulled proximally through the plurality of retaining arms 120, the plurality of retaining arms 120 may be deflectable radially inward to disengage from the proximal tubular mounting portion 210 such that proximal axial translation of the elongate shaft 100 relative to the proximal tubular mounting portion 210 is permitted. FIG. 9 illustrates the elongate shaft 100 axially translated relative to the proximal tubular mounting portion 210 and/or the occlusive medical device 200, wherein when the release wire 130 is in the proximal released position and the plurality of retaining arms 120 is deflected radially inward and/or disengaged from the proximal tubular mounting portion 210, the occlusive medical device 200 may be released from the elongate shaft 100.

In another alternative configuration illustrated in FIGS. 10-13, an occlusive medical device system may include several features and/or elements similar to the occlusive medical device system described above, including a microcatheter 50 configured to navigate within the vasculature, an elongate shaft 100 slidably disposed within a lumen of the microcatheter 50, an occlusive medical device 300 configured to occlude fluid flow through a vessel lumen, and a release wire 130 slidably disposed within a lumen 102 of the elongate shaft 100.

Similar to above, the elongate shaft 100 may include the lumen 102 extending through a tubular body portion of the elongate shaft 100 from a proximal end of the elongate shaft 100 to a distal end of the elongate shaft 100. In some embodiments, the elongate shaft 100 may be a catheter, a hypotube, or other similar tubular structure. Structure present at the proximal end of the elongate shaft 100 may be similar to that described above—the securement member 140, for example.

Additionally, the occlusive medical device system may include a microcatheter 50 sized and configured to navigate a vasculature and/or to deliver the occlusive medical device 300 to a treatment site within the vasculature, for example an artery or a vein. The elongate shaft 100 and the occlusive medical device 300 may be slidably disposed within the lumen of the microcatheter 50. In some embodiments, the microcatheter 50 may facilitate percutaneous delivery of the occlusive medical device 300 to the vasculature and/or the treatment site.

The occlusive medical device 300 may be releasably connected to the elongate shaft 100 by the release wire 130. The release wire 130 may be slidably disposed within the lumen 102 of the elongate shaft 100 and axially translatable between a distal engagement position and a proximal released position. The release wire 130 may have a distal engagement portion 132 and a non-linear distal retention portion 134 disposed distal of and extending distally from the distal engagement portion 132. The release wire 130 may releasably secure the occlusive medical device 300 to the distal end of the elongate shaft 100 when the release wire 130 is disposed within at least a portion of the occlusive medical device 300.

Figure 10:
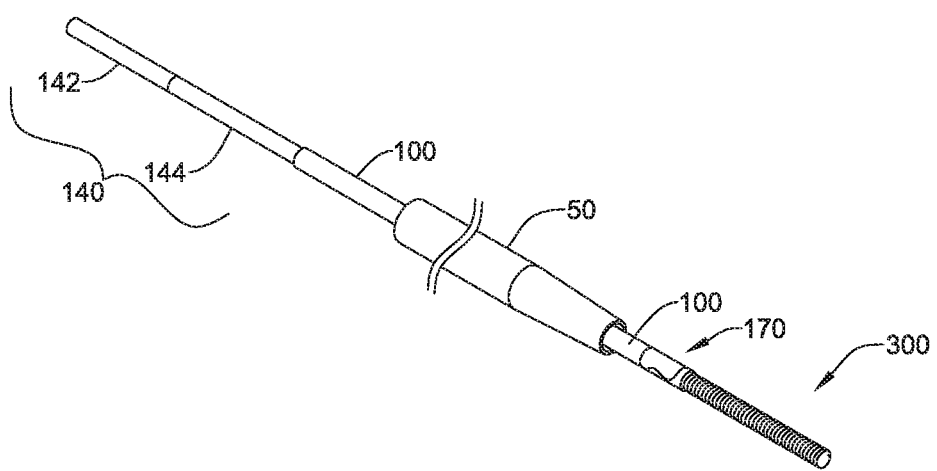
FIG. 10 illustrates an example occlusive medical device system including an occlusive medical device in a delivery configuration.
Figure 11:
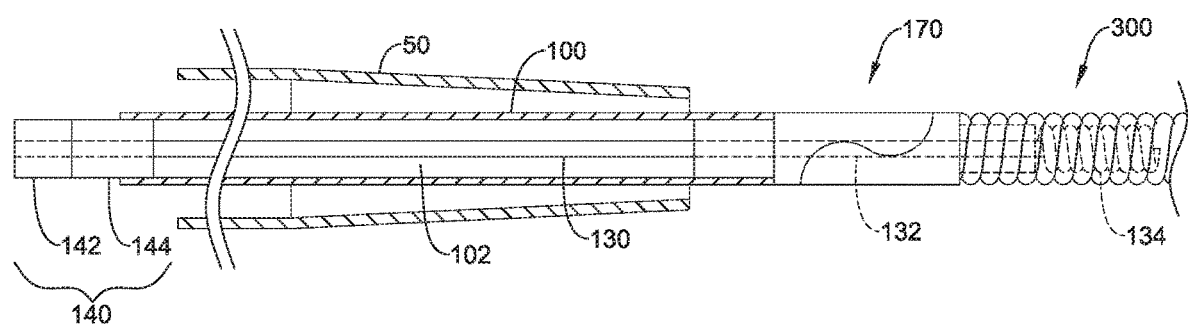
FIGS. 11-13 illustrate the release of the occlusive medical device of FIG. 10.
Figure 12:
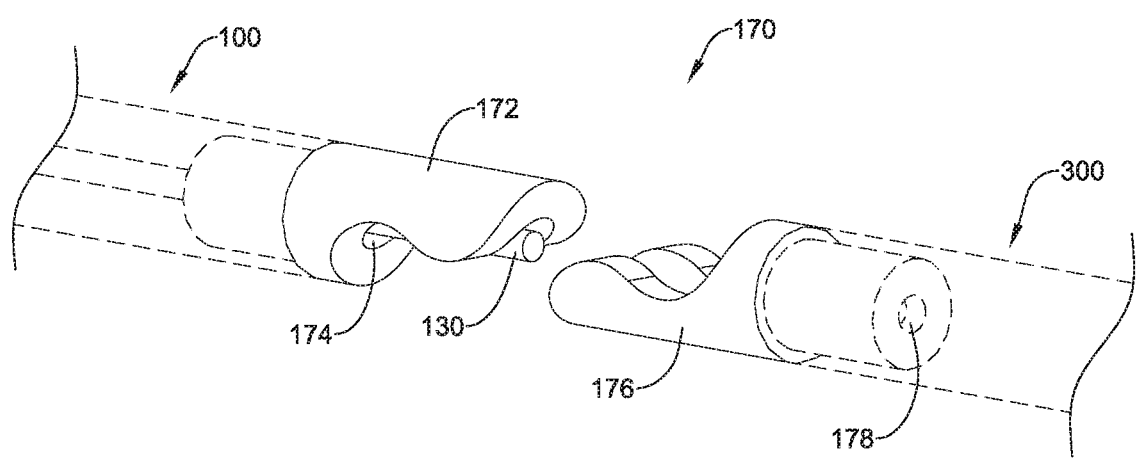
Figure 13:
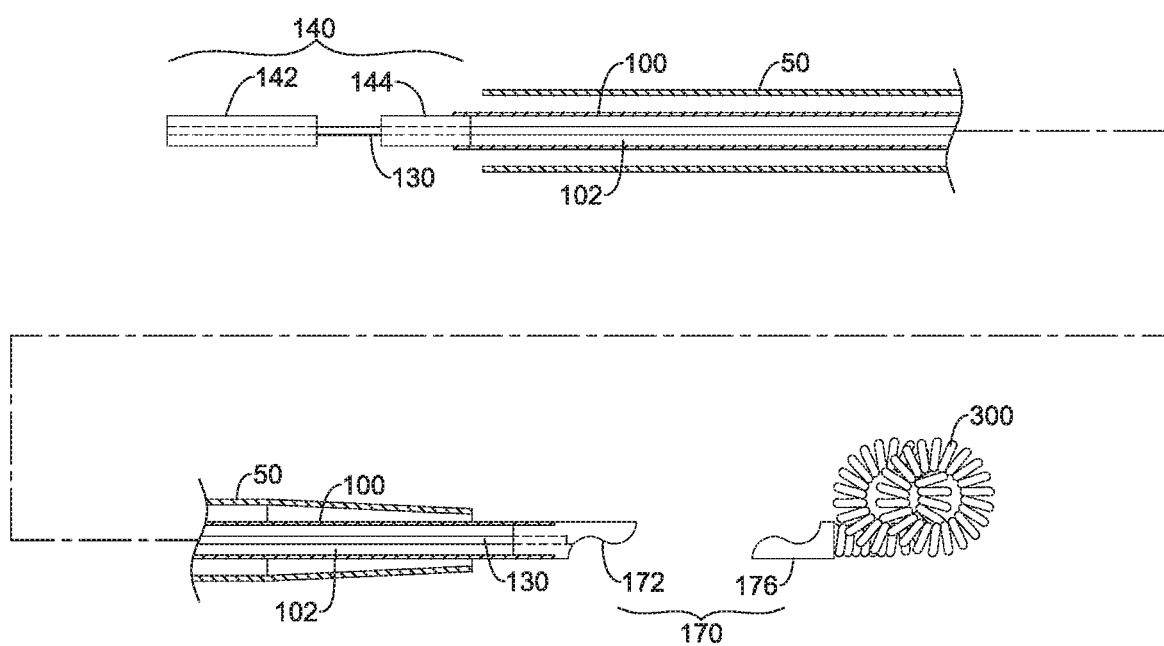

In some embodiments, the occlusive medical device 300 may include a coiled member configured to assume a first shape when connected to the elongate shaft 100 (e.g., FIGS. 10-11) and a second shape when disconnected from the elongate shaft 100 (e.g., FIG. 13). In at least some embodiments, the occlusive medical device 300 may be configured to shift between an elongated delivery configuration (for example, when connected to the elongate shaft 100) as seen in FIGS. 10-11, and a deployed configuration (for example, when disconnected from the elongate shaft 110) as seen in FIG. 13. In some embodiments, the occlusive medical device 300 may be configured to assume a different shape after being released from the elongate shaft 100. Some suitable but non-limiting materials for the occlusive medical device 300, for example metallic materials, polymer materials, composite materials, shape memory materials, etc., are described below.

In some embodiments, the occlusive medical device 300 may include a plurality of fibers and/or a fabric or woven material disposed within and/or attached to individual coil windings of the occlusive medical device 300. The plurality of fibers and/or the fabric or woven material disposed within, attached to, and or embedded within individual coil windings of the occlusive medical device 300 may be configured to enhance coagulation and/or occlusion of the vasculature (e.g., the artery, vein, etc.) and/or the treatment site.

In some embodiments, the occlusive medical device system may include an attachment mechanism 170 disposed between the distal end of the elongate shaft 100 and a proximal end of an occlusive medical device 300, as seen in FIGS. 10-11 for example. The attachment mechanism 170, shown in greater detail in FIG. 12, may comprise a first part 172 having a first longitudinal lumen 174 configured to slidably receive the release wire 130 therein, and a second part 176 having a second longitudinal lumen 178 configured to slidably receive the release wire 130 therein. The first part 172 of the attachment mechanism 170 may be fixedly attached to the distal end of the elongate shaft 100, and in at least some embodiments may be considered a portion of the elongate shaft 100. The second part 176 of the attachment mechanism 170 may be fixedly attached to the proximal end of the occlusive medical device 300, and in at least some embodiments may be considered a portion of the occlusive medical device 300.

In some embodiments, the first part 172 of the attachment mechanism 170 and the second part 176 of the attachment mechanism 170 may be configured to interlock with each other such that relative axial translation between the first part 172 of the attachment mechanism 170 and the second part 176 of the attachment mechanism 170 is prevented when a face of the first part 172 of the attachment mechanism 170 abuts and/or engages a face of the second part 176 of the attachment mechanism 170 and the first longitudinal lumen 174 of the first part 172 of the attachment mechanism 170 is aligned coaxially with the second longitudinal lumen 178 of the second part 176 of the attachment mechanism 170.

Additionally, in some embodiments, the first part 172 of the attachment mechanism 170 and the second part 176 of the attachment mechanism 170 may be configured to interlock with each other such that relative lateral translation between the first part 172 of the attachment mechanism 170 and the second part 176 of the attachment mechanism 170 is prevented when a face of the first part 172 of the attachment mechanism 170 abuts and/or engages a face of the second part 176 of the attachment mechanism 170, the first longitudinal lumen 174 of the first part 172 of the attachment mechanism 170 is aligned coaxially with the second longitudinal lumen 178 of the second part 176 of the attachment mechanism 170, and the release wire 130 is slidably engaged with the first longitudinal lumen 174 of the first part 172 of the attachment mechanism 170 and the second longitudinal lumen 178 of the second part 176 of the attachment mechanism 170.

Briefly turning back to FIG. 11, when the release wire 130 is in the distal engagement position, the non-linear distal retention portion 134 is disposed distal of the second part 176, and the non-linear distal retention portion 134 defines a maximum outer extent greater than an inner diameter of the second longitudinal lumen 178 and/or the first longitudinal lumen 174.

In use, the microcatheter 50 of the occlusive medical device system may be inserted into a patient's anatomy and/or vasculature and a distal end guided and/or advanced to a location adjacent a treatment site. The occlusive medical device 300 disposed at the distal end of the elongate shaft 100 may be inserted into a proximal end of the lumen disposed within the microcatheter 50 and advanced through the microcatheter 50 to the treatment site. In some embodiments, the occlusive medical device 300 may be disposed within the lumen of the microcatheter 50 proximate to the distal end of the elongate shaft 100. In some embodiments, the occlusive medical device 300 may be disposed within the lumen of the microcatheter 50 proximate to the distal end of the elongate shaft 100 prior to use and/or prior to inserting the microcatheter 50 into the patient's anatomy and/or vasculature.

When ready to deploy the occlusive medical device 300 at the treatment site, the elongate shaft 100 may be advanced and/or translated distally relative to the microcatheter 50 until the occlusive medical device 300 is exposed and/or disposed distal of the microcatheter 50. The elongate shaft 100 may have sufficient length that the proximal end of the elongate shaft 100 and/or the securement member 140 remains proximal of (e.g., extends proximally from) the microcatheter 50 when the occlusive medical device 300 is disposed distal of the microcatheter 50. In use, the elongate shaft 100 and the microcatheter 50 may have sufficient length to reach from the treatment site to a position outside of the patient where the occlusive medical device system may be manipulated by an operator (e.g., clinician, physician, user, etc.).

The operator of the occlusive medical device system may then place a first hand on the distal portion 144 of the securement member 140 and a second hand on the proximal portion 142 of the securement member 140. The proximal portion 142 of the securement member 140 may be configured to disengage from the distal portion 144 of the securement member 140 at a location proximal of a proximal end of the microcatheter 50 when the occlusive medical device 300 is disposed distal of the microcatheter 50. In at least some embodiments, the proximal portion 142 of the securement member 140 may be disengaged from the distal portion 144 of the securement member 140 by bending, twisting, and/or pulling the proximal portion 142 of the securement member 140 relative to the distal portion 144 of the securement member 140. In some embodiments, disengaging the proximal portion 142 of the securement member 140 from the distal portion 144 of the securement member 140 may include moving the proximal portion 142 of the securement member 140 relative to the distal portion 144 of the securement member 140 to separate the proximal portion 142 of the securement member 140 from the distal portion 144 of the securement member 140. In some embodiments, disengaging the proximal portion 142 of the securement member 140 from the distal portion 144 of the securement member 140 may include using an external device (e.g., a torque device, an external handle, etc.) to move the proximal portion 142 of the securement member 140 relative to the distal portion 144 of the securement member 140.

When the proximal portion 142 of the securement member 140 is disengaged and/or separated from the distal portion 144 of the securement member 140, the release wire 130 may be translated in a proximal direction relative to the elongate shaft 110 and/or the occlusive medical device 300 to release the second part 176 of the attachment mechanism 170 and/or the occlusive medical device 300 from the first part 172 of the attachment mechanism 170 and/or the elongate shaft 100 (e.g., to release the occlusive medical device 300 from the distal end of the elongate shaft 100). When the release wire 130 is translated and/or withdrawn proximally relative to the elongate shaft 100 and/or the occlusive medical device 300, the occlusive medical device 300 is released from the distal end of the elongate shaft 100 and shifts from the first shape and/or the elongated delivery configuration to the second shape and/or the deployed configuration, as seen in FIG. 13 for example.

In some embodiments, the release wire 130 may include one or more indicators disposed proximate the proximal end of the release wire 130 configured to show how much of the release wire 130 has been withdrawn and/or configured to communicate to a user of the occlusive medical device system when the occlusive medical device 300 has been released. The one or more indicators may include lines, detents, colors, notches, or other suitable indicators. The one or more indicators, if visible, may be seen between the proximal portion 142 of the securement member 140 and the distal portion 144 of the securement member 140 after the proximal portion 142 of the securement member 140 has been disengaged from the distal portion 144 of the securement member 140 at the joint.

The materials that can be used for the various components of the occlusive medical device system, the microcatheter 50, the elongate shaft 100, the release wire 130, the securement member 140, the occlusive medical device 200/300, the proximal tubular mounting portion 210, and/or the expandable occlusive element 230, etc. (and/or other systems or components disclosed herein) and the various elements thereof disclosed herein may include those commonly associated with medical devices. For simplicity purposes, the following discussion makes reference to the occlusive medical device system, the microcatheter 50, the elongate shaft 100, the release wire 130, the securement member 140, the occlusive medical device 200/300, the proximal tubular mounting portion 210, and/or the expandable occlusive element 230, etc. However, this is not intended to limit the devices and methods described herein, as the discussion may be applied to other elements, members, components, or devices disclosed herein, such as, but not limited to, the plurality of retaining arms 120, the protrusions 122, the distal engagement portion 132, the distal retention portion 134, the proximal portion 142, the distal portion 144, the attachment mechanism 170, the first part 172, and second part 176, the support frame 232, the occlusive membrane 234, etc. and/or elements or components thereof.

In some embodiments, the occlusive medical device system, the microcatheter 50, the elongate shaft 100, the release wire 130, the securement member 140, the occlusive medical device 200/300, the proximal tubular mounting portion 210, and/or the expandable occlusive element 230, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive medical device system, the microcatheter 50, the elongate shaft 100, the release wire 130, the securement member 140, the occlusive medical device 200/300, the proximal tubular mounting portion 210, and/or the expandable occlusive element 230, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive medical device system, the microcatheter 50, the elongate shaft 100, the release wire 130, the securement member 140, the occlusive medical device 200/300, the proximal tubular mounting portion 210, and/or the expandable occlusive element 230, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive medical device system, the microcatheter 50, the elongate shaft 100, the release wire 130, the securement member 140, the occlusive medical device 200/300, the proximal tubular mounting portion 210, and/or the expandable occlusive element 230, etc. to achieve the same result.

In some embodiments, a degree of Magnetic Resonance Imaging (MRI) compatibility is imparted into the occlusive medical device system, the microcatheter 50, the elongate shaft 100, the release wire 130, the securement member 140, the occlusive medical device 200/300, the proximal tubular mounting portion 210, and/or the expandable occlusive element 230, etc. For example, the occlusive medical device system, the microcatheter 50, the elongate shaft 100, the release wire 130, the securement member 140, the occlusive medical device 200/300, the proximal tubular mounting portion 210, and/or the expandable occlusive element 230, etc., and/or components or portions thereof, may be made of a material that does not substantially distort the image and create substantial artifacts (e.g., gaps in the image). Certain ferromagnetic materials, for example, may not be suitable because they may create artifacts in an MM image. The occlusive medical device system, the microcatheter 50, the elongate shaft 100, the release wire 130, the securement member 140, the occlusive medical device 200/300, the proximal tubular mounting portion 210, and/or the expandable occlusive element 230, etc., or portions thereof, may also be made from a material that the Mill machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive medical device system, the microcatheter 50, the elongate shaft 100, the release wire 130, the securement member 140, the occlusive medical device 200/300, the proximal tubular mounting portion 210, and/or the expandable occlusive element 230, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive medical device system, the microcatheter 50, the elongate shaft 100, the release wire 130, the securement member 140, the occlusive medical device 200/300, the proximal tubular mounting portion 210, and/or the expandable occlusive element 230, the occlusive membrane 234, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyl s, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive medical device system, the microcatheter 50, the elongate shaft 100, the release wire 130, the securement member 140, the occlusive medical device 200/300, the proximal tubular mounting portion 210, and/or the expandable occlusive element 230, the occlusive membrane 234, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An occlusive medical device system, comprising:
   an elongate shaft having a tubular body portion, a lumen extending longitudinally through the tubular body portion, and a plurality of retaining arms extending distally from the tubular body portion;
   an occlusive medical device configured to occlude fluid flow through a vessel lumen, the occlusive medical device including a proximal tubular mounting portion fixed to an expandable occlusive element; and
   a release wire disposed within the lumen of the tubular body portion and axially translatable between a distal engagement position and a proximal released position, the release wire having a distal engagement portion and a distal retention portion distal of the distal engagement portion;
   wherein the plurality of retaining arms extends into the proximal tubular mounting portion;
   wherein the distal engagement portion of the release wire is configured to engage the plurality of retaining arms in the distal engagement position, thereby urging the plurality of retaining arms radially outward into releasable engagement with the proximal tubular mounting portion of the occlusive medical device,
   wherein the distal retention portion includes a maximum outer extent greater than an inner diameter of the lumen in the distal engagement position;
   wherein when the release wire is in the proximal released position, the plurality of retaining arms is deflectable radially inward to disengage from the proximal tubular mounting portion.

2. The occlusive medical device system of claim 1, wherein the distal retention portion is configured to axially translate through the lumen from the distal engagement position to the proximal released position.

3. The occlusive medical device system of claim 1, wherein the distal retention portion is non-linear.

4. The occlusive medical device system of claim 1, wherein the distal retention portion comprises a helical coil.

5. The occlusive medical device system of claim 4, wherein the helical coil has a closed pitch.

6. The occlusive medical device system of claim 1, wherein the proximal tubular mounting portion includes a plurality of apertures configured to engage the plurality of retaining arms when the release wire is in the distal engagement position.

7. The occlusive medical device system of claim 6, wherein each of the plurality of retaining arms includes a protrusion extending radially outward from an outer surface of its respective retaining arm.

8. The occlusive medical device system of claim 7, wherein each protrusion of the plurality of retaining arms engages one of the plurality of apertures of the proximal tubular mounting portion when the release wire is in the distal engagement position.

9. An occlusive medical device system, comprising:
   a microcatheter configured to navigate a vasculature;
   an elongate shaft having a tubular body portion, a lumen extending longitudinally through the tubular body portion, and a plurality of retaining arms extending distally from the tubular body portion;
   an occlusive medical device configured to occlude fluid flow through a vessel lumen, the occlusive medical device including a proximal tubular mounting portion fixed to an expandable occlusive element; and
   a release wire disposed within the lumen of the tubular body portion and axially translatable between a distal engagement position and a proximal released position, the release wire having a distal engagement portion and a distal retention portion distal of the distal engagement portion;
   wherein the plurality of retaining arms extends into the proximal tubular mounting portion;
   wherein the distal engagement portion of the release wire is configured to engage the plurality of retaining arms in the distal engagement position, thereby urging the plurality of retaining arms radially outward into releasable engagement with the proximal tubular mounting portion of the occlusive medical device,
   wherein the distal retention portion includes a maximum outer extent greater than an inner diameter of the lumen in the distal engagement position;
   wherein when the release wire is in the proximal released position, the plurality of retaining arms is deflectable radially inward to disengage from the proximal tubular mounting portion;
   wherein the elongate shaft is slidably disposed within a lumen of the microcatheter.

10. The occlusive medical device system of claim 9, wherein the occlusive medical device is expandable from a delivery configuration to a deployed configuration.

11. The occlusive medical device system of claim 10, wherein the occlusive medical device is disposed within a distal end of the lumen of the microcatheter in the delivery configuration.

12. The occlusive medical device system of claim 10, wherein when the release wire is in the proximal released position and the plurality of retaining arms is disengaged from the proximal tubular mounting portion, the occlusive medical device is released from the elongate shaft.

* * * * *